(12) United States Patent
Kudo et al.

(10) Patent No.: US 8,603,103 B2
(45) Date of Patent: Dec. 10, 2013

(54) INTRAOCULAR LENS INSERTION DEVICE

(75) Inventors: Kazunori Kudo, Saku (JP); Masahiro Noda, Toda (JP)

(73) Assignee: Hoya Corporation, Tokyo (JP)

( * ) Notice: Subject to any disclaimer, the term of this patent is extended or adjusted under 35 U.S.C. 154(b) by 26 days.

(21) Appl. No.: 13/143,322

(22) PCT Filed: Jan. 5, 2010

(86) PCT No.: PCT/JP2010/050029
§ 371 (c)(1),
(2), (4) Date: Aug. 10, 2011

(87) PCT Pub. No.: WO2010/079780
PCT Pub. Date: Jul. 15, 2010

(65) Prior Publication Data
US 2011/0288557 A1    Nov. 24, 2011

(30) Foreign Application Priority Data
Jan. 7, 2009    (JP) ................................. 2009-001493

(51) Int. Cl.
*A61F 9/007*    (2006.01)
(52) U.S. Cl.
USPC .......................................................... 606/107
(58) Field of Classification Search
USPC .................................. 606/107; 623/6.12, 6.11
See application file for complete search history.

(56) References Cited

U.S. PATENT DOCUMENTS

| | | |
|---|---|---|
| 2,761,446 A | 9/1956 | Reed |
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |

(Continued)

FOREIGN PATENT DOCUMENTS

| | | |
|---|---|---|
| DE | 3610925 | 10/1987 |
| DE | 4110278 | 10/1992 |
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 4-212350 A | 8/1992 |

(Continued)

OTHER PUBLICATIONS

Machine translation WO 2008/149795; WIPO Patentscope Jan. 28, 2013.*

(Continued)

*Primary Examiner* — Elizabeth Houston
(74) *Attorney, Agent, or Firm* — Henricks, Slavin & Holmes LLP

(57) ABSTRACT

There is provided an intraocular lens insertion device capable of appropriately regulating the motion of a rear supporting portion during a process of moving an intraocular lens, and reducing the possibility of reoperation being required after the intraocular lens is inserted into an eye. An intraocular lens insertion device 1 comprises a main body 2, and a slider 3 and a plunger 4 that are attached to the main body 2. Further, the intraocular lens insertion device 1 is of a preset type in which an intraocular lens 5 is placed inside the main body 2 in advance. The slider 3 includes a first abutting portion 21 for pushing up a supporting portion 7 (rear supporting portion 7a) arranged on a rear side of an optical part 6 with respect to a lens advancement axis A, and second abutting portions 22a, 22b abutting against an outer edge of a rear portion of the optical part 6.

13 Claims, 9 Drawing Sheets

(56) References Cited

U.S. PATENT DOCUMENTS

| | | |
|---|---|---|
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,607,537 B1 | 8/2003 | Binder |
| 6,629,979 B1 | 10/2003 | Feingold et al. |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |

(56) References Cited

U.S. PATENT DOCUMENTS

| | | |
|---|---|---|
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi |
| 2004/0111094 A1 | 6/2004 | Meyer |
| 2004/0117012 A1 | 6/2004 | Vincent |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0125000 A1 | 6/2005 | Tourrette et al. |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0229633 A1 | 10/2006 | Shepherd |
| 2006/0293694 A1 | 12/2006 | Futamura |
| 2008/0033449 A1 | 2/2008 | Cole et al. |
| 2008/0058830 A1 | 3/2008 | Cole |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0161049 A1 | 6/2010 | Inoue |
| 2010/0185206 A1 | 7/2010 | Ichinohe et al. |
| 2010/0217273 A1* | 8/2010 | Someya et al. ............... 606/107 |
| 2010/0286704 A1 | 11/2010 | Ichinohe et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |
| 2013/0226193 A1 | 8/2013 | Kudo et al. |
| 2013/0245635 A1 | 9/2013 | Inoue |

FOREIGN PATENT DOCUMENTS

| | | |
|---|---|---|
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-24854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO 2008/149795 * | 12/2008 |
| WO | WO 2008/149795 A | 12/2008 |
| WO | WO2008149794 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

OTHER PUBLICATIONS

PCT International Search Report dated Feb. 2, 2010 for PCT App. Ser. No. PCT/JP2010/050029.

* cited by examiner

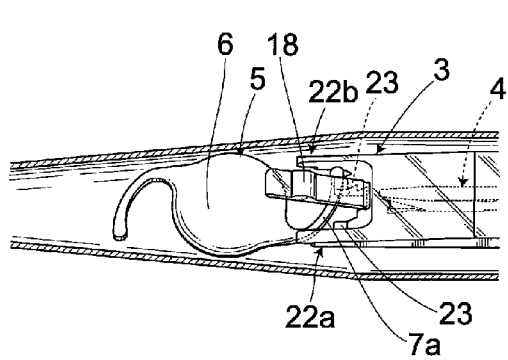
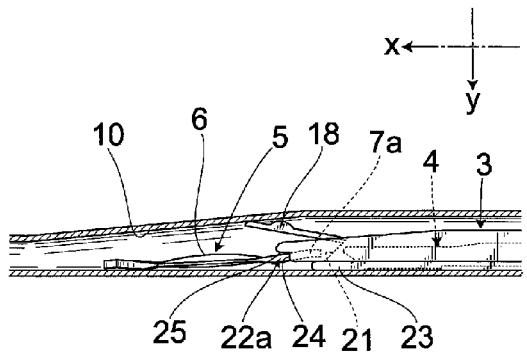
FIG.4A  FIG.4B
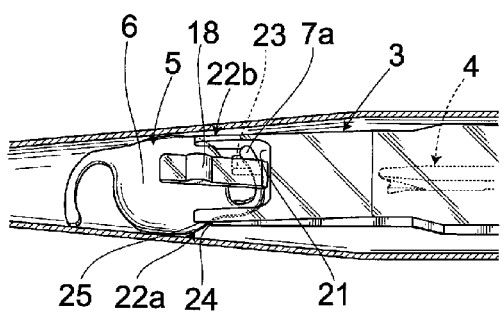
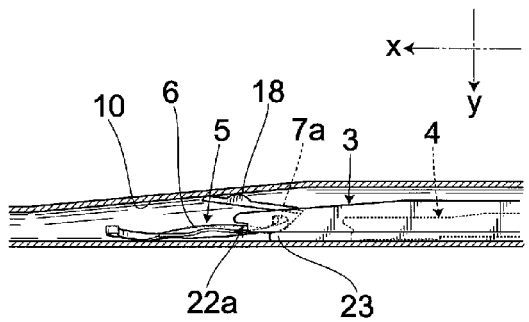
FIG.5A  FIG.5B
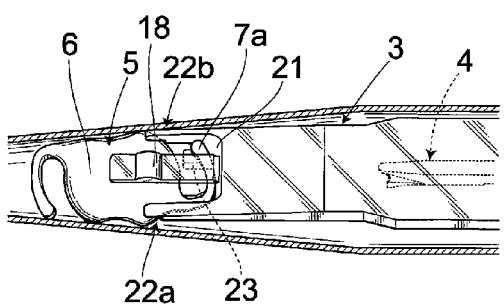
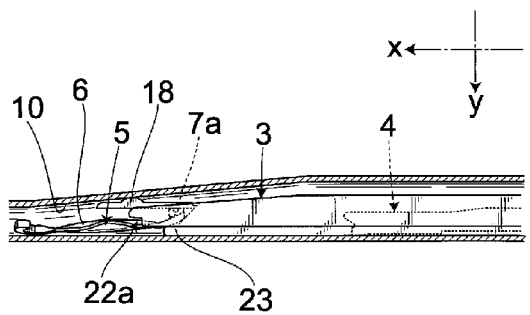
FIG.6A  FIG.6B

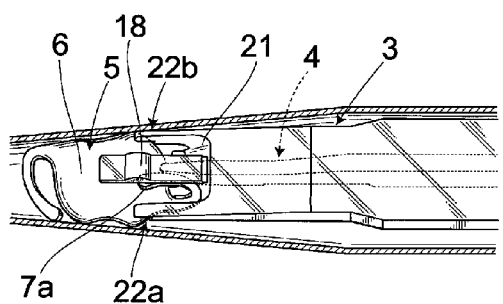 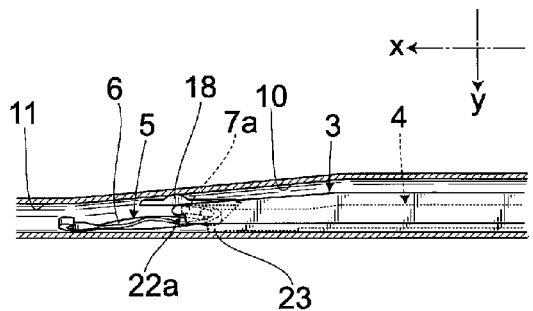
FIG.7A  FIG.7B
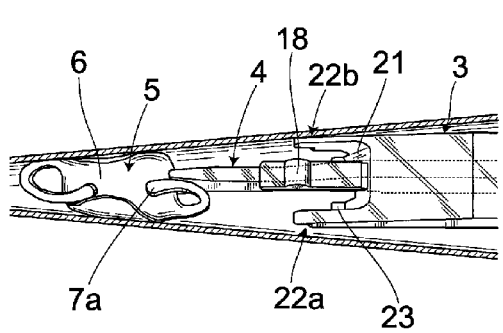 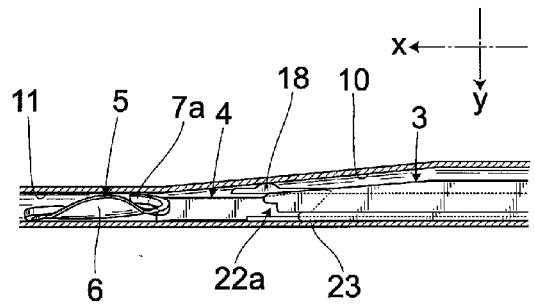
FIG.8A  FIG.8B

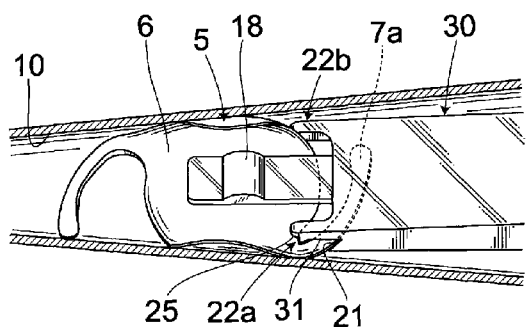
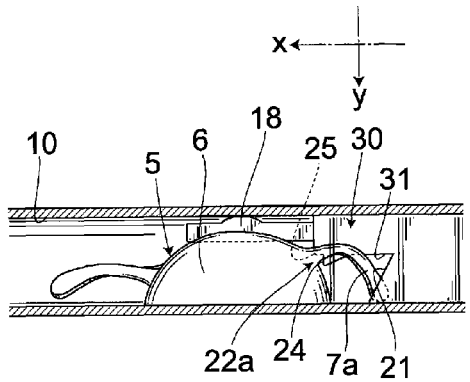
FIG.10A     FIG.10B
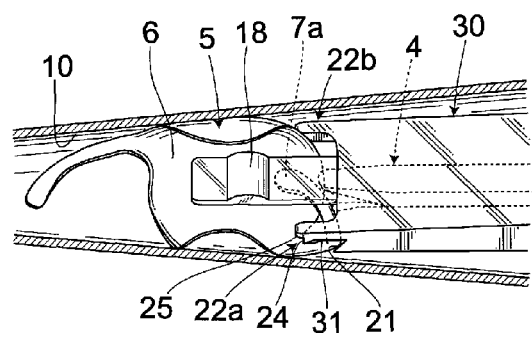
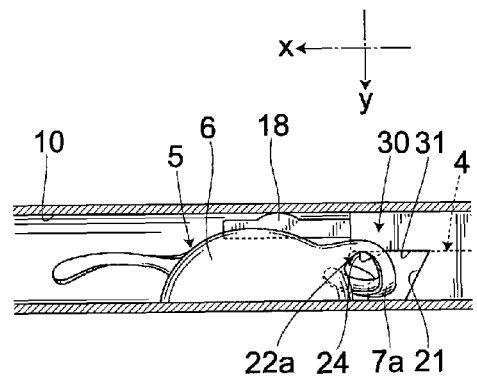
FIG.11A     FIG.11B
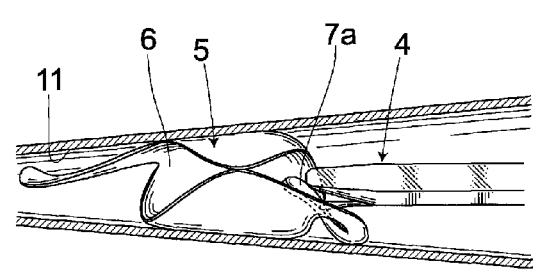
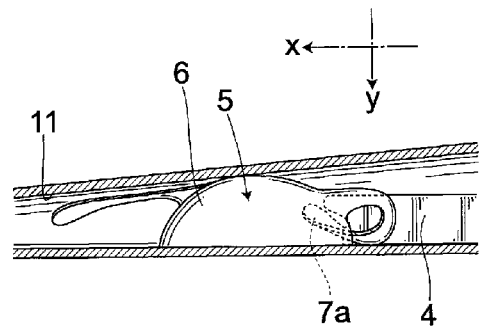
FIG.12A     FIG.12B

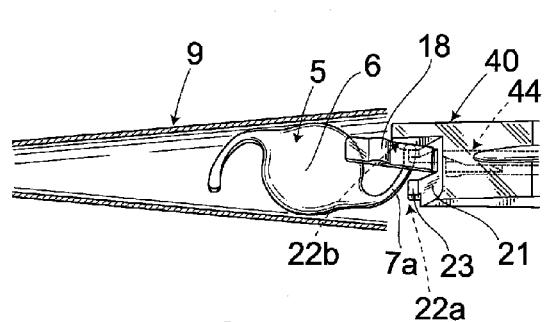
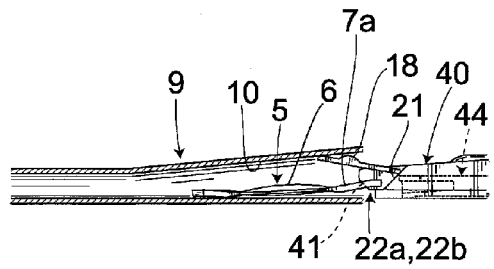
FIG.15A    FIG.15B
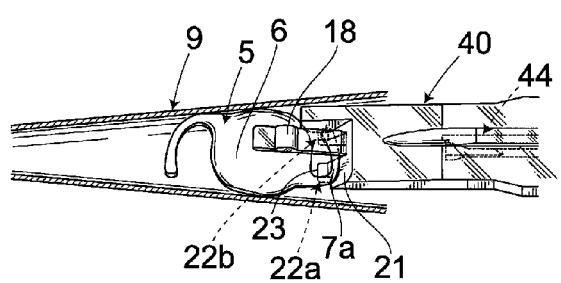
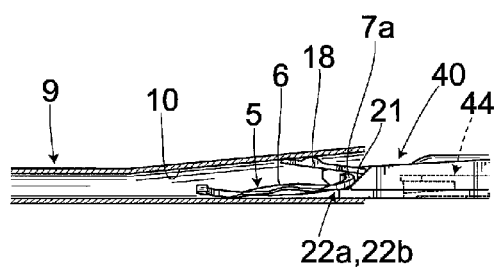
FIG.16A    FIG.16B
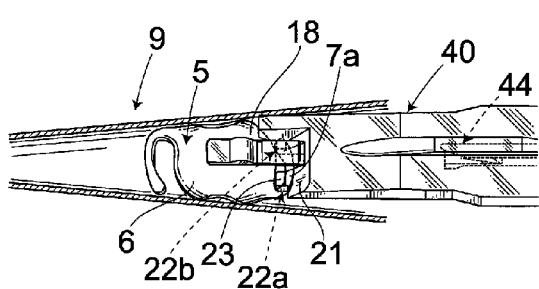
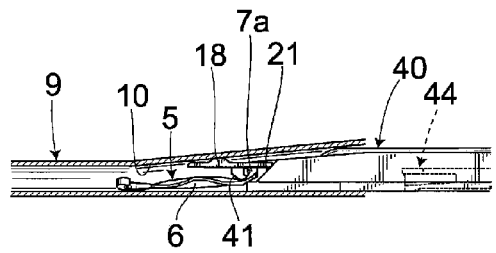
FIG.17A    FIG.17B

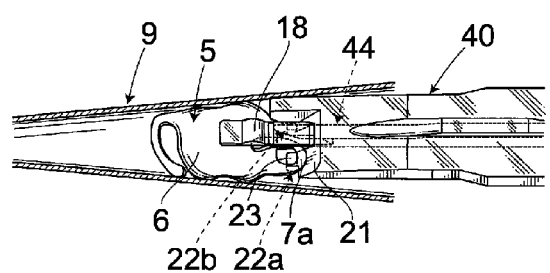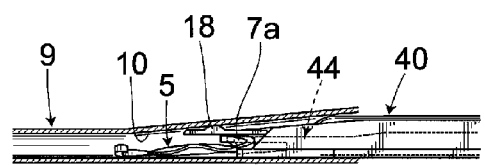
FIG.18A  FIG.18B
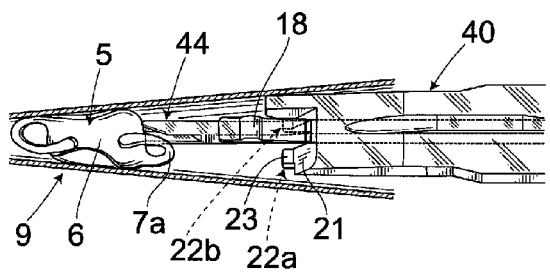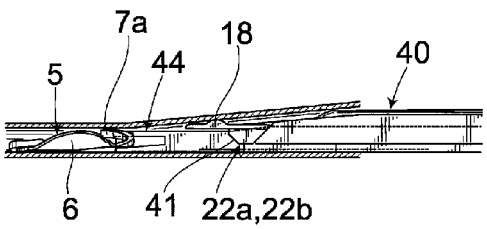
FIG.19A  FIG.19B

INTRAOCULAR LENS INSERTION DEVICE

TECHNICAL FIELD

The present invention relates to an intraocular lens insertion device for inserting an intraocular lens into an eyeball as a substitute of a crystalline lens exenterated through cataract surgery.

BACKGROUND ART

Cataract surgery often involves removing an opacified crystalline lens through phacoemulsification (PEA), and implanting an intraocular lens after the crystalline lens has been removed. Intraocular lenses include hard intraocular lenses whose optical parts are made of hard materials such as PMMA or the like, and soft intraocular lenses whose optical parts are made of soft materials such as silicon elastomer, soft acrylic, hydrogel or the like.

When inserting a hard intraocular lens, there has to be formed on the cornea or the sclera an incision substantially as wide as the diameter of the optical part of the corresponding hard intraocular lens. In contrast, a soft intraocular lens can be inserted through an incision smaller than the diameter of the optical part thereof by allowing the corresponding optical part to be folded.

An intraocular lens is preferably inserted through a small incision in order to reduce the possibilities of corneal astigmatism and infection after the surgery. In this sense, soft intraocular lenses tend to be preferred nowadays. Types of soft intraocular lens include: a soft intraocular lens having an optical part made of a soft material and supporting portions made of a hard material such as PMMA or the like (the supporting portions of this type of intraocular lens are usually two thin filamentary members); a soft intraocular lens whose optical part and supporting portions are made of a same soft material (the supporting portions of this type are usually plate members); or a soft intraocular lens employing a plurality of thin strips as supporting portions, and the like.

Further, in order to insert an intraocular lens into an eye, there has also been used a dedicated intraocular lens insertion device having a structure for introducing the intraocular lens into the eye through an elongated tube. This type of intraocular lens insertion device allows an intraocular lens to be inserted through an incision smaller than 3mm.

Furthermore, in recent years, there has been developed a type of intraocular lens insertion device which has an intraocular lens placed therein in advance and can be packaged and stored, in order to exclude the possibilities of bacteria contamination and errors in operation at the time of handling the intraocular lens (e.g., patent document 1).

However, this type of intraocular lens insertion device may cause a supporting portion (referred to as a rear supporting portion, hereunder) arranged on a rear side with respect to a lens advancement axis to slip in between a plunger for pushing out the intraocular lens and a passage inner wall surface of the insertion device, or be tangled with the corresponding plunger, during a process of moving the intraocular lens. These problems are particularly noticeable with soft intraocular lenses employing thin filamentary members as supporting portions and intraocular lenses employing thin strips as supporting portions.

Further, this type of intraocular lens insertion device may cause the rear supporting portion to be stretched during the process of moving the intraocular lens. Accordingly, the corresponding rear supporting portion may then be left outside an eye ball at the time of performing insertion through a small incision on the eyeball, thereby requiring an additional operation for inserting such rear supporting portion into the eye ball after pushing out the intraocular lens with the plunger, and thus making the surgery troublesome.

In this sense, when using an intraocular lens insertion device to insert an intraocular lens into an eye, the motion of the rear supporting portion of the intraocular lens has to be appropriately regulated during the process of moving the intraocular lens.

In view of the aforementioned problems, there has been disclosed a device in which a clearance is formed on a front end side portion of a plunger, for allowing the rear supporting portion to be kept therein and thus preventing the same from being damaged (e.g., patent document 2). Further, there has been disclosed a device in which a rear supporting portion receiving passage for receiving the rear supporting portion is provided on a lower side portion of a plunger (e.g., patent document 3). Furthermore, there has also been disclosed a device in which the rear supporting portion is pushed up on a lump portion by means of a plunger, thereby allowing the corresponding haptic to be bended upward and eventually positioned higher than an IOL (e.g., patent document 4). Accordingly, all the devices disclosed in the aforementioned patent documents serve to reduce holding pressures applied to the rear supporting portions of intraocular lenses employing thin filaments or strips as supporting portions.

Reference:

Patent document 1: WO2007/037223
Patent document 2: Japanese Unexamined Patent Application Publication (Translation of PCT Application) No. 1999-506357
Patent document 3: U.S. Pat. No. 6,733,507
Patent document 4: Japanese Unexamined Patent Application Publication No. 2004-351196

DISCLOSURE OF THE INVENTION

Problem to be Solved by the Invention

However, according to the patent documents 2 and 3, the rear supporting portion received in the clearance formed on the front end side portion of the plunger and in the rear supporting portion receiving passage is stretched, thereby still incurring a problem in which the corresponding rear supporting portion may be left outside a small incision formed on an eye ball when inserting an intraocular lens therethrough. Particularly, with regard to intraocular lenses employing thin strips as supporting portions, reoperation is often troublesome because the corresponding supporting portions are composed of soft members that are thick in sizes. Further, according to the patent document 4, the supporting portion is pushed by a small plunger front end matched to a nozzle front end with a small aperture diameter, thus causing the rear supporting portion to be compressed into an unexpected shape when bending the supporting portion upward so as to position the same higher than an optical part or when allowing an intraocular lens to pass through a passage.

Here, in view of the aforementioned problems, it is an object of the present invention to provide an intraocular lens insertion device capable of appropriately regulating the motion of a rear supporting portion during a process of moving an intraocular lens, and reducing the possibility of reoperation being required after the intraocular lens has been inserted into an eye.

Means for Solving the Problem

The invention according to a first aspect of the present invention is an intraocular lens insertion device comprising: a lens placement section for placing an intraocular lens having an optical part and one or more supporting portions provided on an outer edge of the optical part; a transition section for deforming the intraocular lens; a nozzle section for releasing the intraocular lens; a slider for pushing out the intraocular lens placed in the lens placement section; and a plunger for releasing the intraocular lens pushed out by the slider from the nozzle section, in which the slider includes: a first abutting portion for pushing up a supporting portion disposed in a rear direction of a lens advancement axis; and one or more second abutting portions abutting against an outer edge of a rear portion of the intraocular lens.

According to the invention described in a second aspect of the present invention, the second abutting portions are provided outside the first abutting portion with respect to the lens advancement axis.

According to the invention described in a third aspect of the present invention, the first abutting portion slants downward in a lens advancement direction.

According to the invention described in a fourth aspect of the present invention, at least one of the second abutting portions includes: an x-direction abutting surface substantially perpendicular to a surface of the optical part; and a y-direction abutting surface substantially parallel with the surface of the optical part.

The invention according to a fifth aspect of the present invention comprises a guiding portion for guiding the outer edge of the optical part to the second abutting portions.

According to the invention described in a sixth aspect of the present invention, the second abutting portions are provided as a left-right pair centered about the lens advancement axis.

Effects of the invention

According to the present invention, the first abutting portion provided on the slider serves to push up the supporting portion arranged on the rear side with respect to the lens advancement axis, thereby allowing the motion of the rear supporting portion to be appropriately regulated during the process of moving the intraocular lens, and thus reducing the possibility of reoperation being required after the intraocular lens is inserted into the eye.

BRIEF DESCRIPTION OF THE DRAWINGS

FIGS. 4A and 4B are diagrams showing a usage state (1) of the intraocular lens insertion device of the first embodiment of the present invention, in which FIG. 4A is a cross sectional top view, and FIG. 4B is a longitudinal sectional view.

FIGS. 5A and 5B are diagrams showing a usage state (2) of the intraocular lens insertion device of the first embodiment of the present invention, in which FIG. 5A is a cross sectional top view, and FIG. 5B is a longitudinal sectional view.

FIGS. 6A and 6B are diagrams showing a usage state (3) of the intraocular lens insertion device of the first embodiment of the present invention, in which FIG. 6A is a cross sectional top view, and FIG. 6B is a longitudinal sectional view.

FIGS. 7A and 7B are diagrams showing a usage state (4) of the intraocular lens insertion device of the first embodiment of the present invention, in which FIG. 7A is a cross sectional top view, and FIG. 7B is a longitudinal sectional view.

FIGS. 8A and 8B are diagrams showing a usage state (5) of the intraocular lens insertion device of the first embodiment of the present invention, in which FIG. 8A is a cross sectional top view, and FIG. 8B is a longitudinal sectional view.

FIGS. 10A and 10B are diagrams showing a usage state (1) of an intraocular lens insertion device of the second embodiment of the present invention, in which FIG. 10A is a cross sectional top view, and FIG. 10B is a longitudinal sectional view.

FIGS. 11A and 11B are diagrams showing a usage state (2) of the intraocular lens insertion device of the second embodiment of the present invention, in which FIG. 11A is a cross sectional top view, and FIG. 11 B is a longitudinal sectional view.

FIGS. 12A and 12B are diagrams showing a usage state (3) of the intraocular lens insertion device of the second embodiment of the present invention, in which FIG. 12A is a cross sectional top view, and FIG. 12B is a longitudinal sectional view.

FIGS. 15A and 15B are diagrams showing a usage state (1) of an intraocular lens insertion device of the third embodiment of the present invention, in which FIG. 15A is a cross sectional top view, and FIG. 15B is a longitudinal sectional view.

FIGS. 16A and 16B are diagrams showing a usage state (2) of the intraocular lens insertion device of the third embodiment of the present invention, in which FIG. 16A is a cross sectional top view, and FIG. 16B is a longitudinal sectional view.

FIGS. 17A and 17B are diagrams showing a usage state (3) of the intraocular lens insertion device of the third embodiment of the present invention, in which FIG. 17A is a cross sectional top view, and FIG. 17B is a longitudinal sectional view.

FIGS. 18A and 18B are diagrams showing a usage state (4) of the intraocular lens insertion device of the third embodiment of the present invention, in which FIG. 18A is a cross sectional top view, and FIG. 18B is a longitudinal sectional view.

FIGS. 19A and 19B are diagrams showing a usage state (5) of the intraocular lens insertion device of the third embodiment of the present invention, in which FIG. 19A is a cross sectional top view, and FIG. 19B is a longitudinal sectional view.

BEST MODE FOR CARRYING OUT THE INVENTION

1. First Embodiment (1) Basic Structure

An embodiment of the present invention is described hereunder in detail and with reference to the accompanying drawings.

Figure 1:
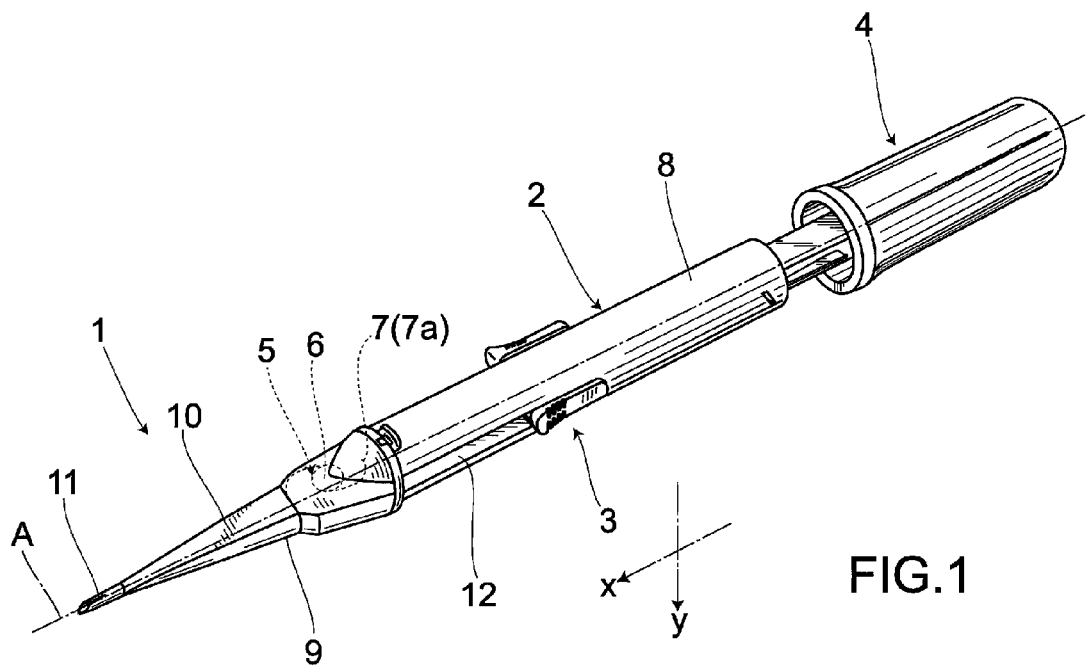
FIG. 1 is a perspective view showing an overall structure of an intraocular lens insertion device of a first embodiment of the present invention.

An intraocular lens insertion device 1 shown in FIG. 1 comprises a main body 2, and a slider 3 and a plunger 4 that are attached to the main body 2. The intraocular lens insertion device 1 is of a preset type in which an intraocular lens 5 is placed inside the main body 2 in advance. Here, the intraocular lens 5 includes an optical part 6 and a pair of supporting portions 7 (or "haptics") provided on an outer edge of the optical part 6. As the supporting portions 7, there can be employed various types of members including, for example, members of a thin strip type.

In the following descriptions, an axis extending through the center of the intraocular lens 5 moving inside the main body 2 is referred to as a lens advancement axis A. Further, a direction to which the intraocular lens 5 moves is referred to as an "advancement direction x," and a downward direction is referred to as a "direction y."

The main body 2 is composed of a base end portion 8 and an insertion tube 9 connected to a front end of the base end portion 8 in the advancement direction x. Although not shown, a lens placement section made of a plate type member is formed on the front end of the base end portion 8 in the advancement direction x. The intraocular lens 5 is placed in the corresponding lens placement section. On side surfaces of the base end portion 8, there are provided slits 12 formed in parallel with the lens advancement axis A and extending to the front end of the base end portion 8. Further, the insertion tube 9 is integrally connected to the front end of the base end portion 8, thereby allowing the intraocular lens 5 placed in the lens placement section of the base end portion 8 to be disposed internally.

The insertion tube 9 comprises a transition section 10 and a nozzle section 11 that are successively disposed along the lens advancement axis A. The transition section 10 is formed into a tapered shape in which an inner wall of the transition section 10 tapers toward a front end thereof, such front end being further communicated with the nozzle section 11. The nozzle section 11 is so formed that an outer shape thereof can be inserted into an incision (not shown).

According to this intraocular lens insertion device 1, the intraocular lens 5 placed in the lens placement section is at first moved to the transition section 10 after being pushed out by the slider 3, thereby allowing the intraocular lens 5 to be reliably folded into a given shape. Next, the intraocular lens 5 is further moved to the nozzle section 11 after being pushed out by the plunger 4, thereby causing the intraocular lens 5 to be folded even smaller, and thus allowing the intraocular lens 5 to be inserted into an eye from a front end of the nozzle section 11. Accordingly, the intraocular lens insertion device 1 allows the intraocular lens 5 to be moved in the advancement direction x in two stages involving successively the slider 3 and the plunger 4, thus causing the intraocular lens 5 to be folded into a given shape and releasing the same to the outside.

(2) Structure of Slider

Figure 2:
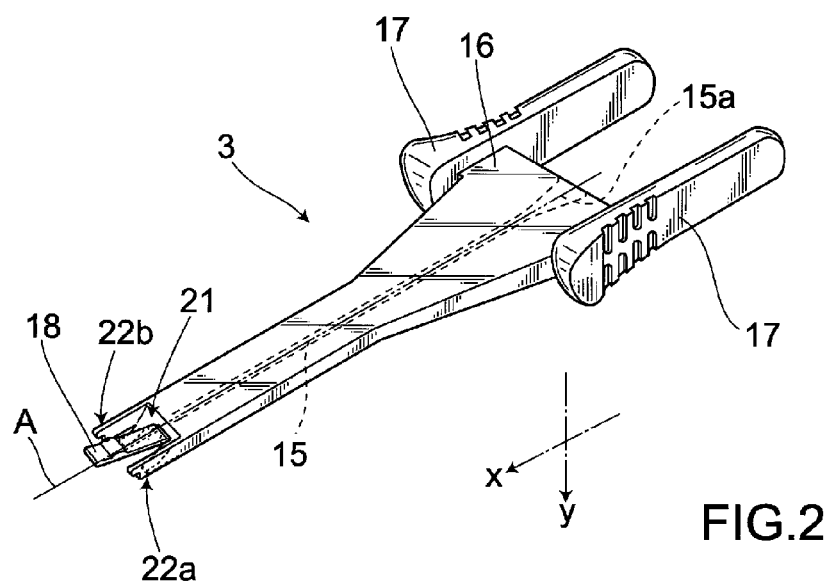
FIG. 2 is a perspective view showing a structure of a slider of the first embodiment of the present invention.

Next, the slider 3 attached to the main body 2 is described. As shown in FIG. 2, the slider 3 servers to push out the intraocular lens 5 placed in the lens placement section to the transition section 10 without imposing a local load thereon, and fold the intraocular lens 5 into the given shape. The slider 3 includes a guiding groove 15, a wing portion 16, operation portions 17 and a lens pressing member 18.

The guiding groove 15 is so configured that the plunger 4 can be supported thereby along the lens advancement axis A. Specifically, the guiding groove 15 allows the plunger 4 to slide, and a front end of the plunger 4 to protrude from a front end of the slider 3. According to the present embodiment, the guiding groove 15 is longitudinally formed over an entire length of a surface of the slider 3 in a manner such that the guiding groove 15 is substantially located in the center of the surface of the slider 3. Accordingly, the guiding groove 15 serves as a groove parallel to the lens advancement axis A. A cross-sectional surface of the guiding groove 15 is substantially formed into a same shape as an outer shape of the plunger 4. A wedge guiding path 15*a* is formed on a base end of the guiding groove 15. In this way, the plunger 4 is allowed to be inserted into the guiding groove 15 formed on the slider 3, and slide within the guiding groove 15 in a longitudinal direction of the slider 3.

The wing portion 16 is inserted into the slits 12 provided on the main body 2, and serves to support the slider 3 along the lens advancement axis A. By inserting the wing portion 16 into the slits 12, the slider 3 is allowed to not only be held in a substantial center portion of the main body 2, but also move along the lens advancement axis A. In this sense, the plunger 4 can also be held in the center portion of the main body 2 and move along the lens advancement axis A, when inserted into the guiding groove 15 formed on the slider 3. The slider 3 can be easily moved by means of the operation portions 17.

The operation portions 17 are provided as a left-right pair centered about the lens advancement axis A. Further, the operation portions 17 are connected to side end portions of the wing portion 16, and protrude from each side of the base end portion 8.

The lens pressing member 18 serves to fold the intraocular lens 5 in a given direction by pressing a surface of the intraocular lens 5 only when the intraocular lens 5 is being pushed out. According to the present embodiment, the lens pressing member 18 serves to press a surface of the intraocular lens 5 to the direction y, thereby causing the intraocular lens 5 to be folded inside the nozzle section 11 with the foregoing surface being folded inwardly, such surface being a front surface when releasing the intraocular lens 5 into the eye. The lens pressing member 18 is made of a strip type member provided on the front end of the slider 3, and is capable of swinging freely to the direction y.

Figure 3:
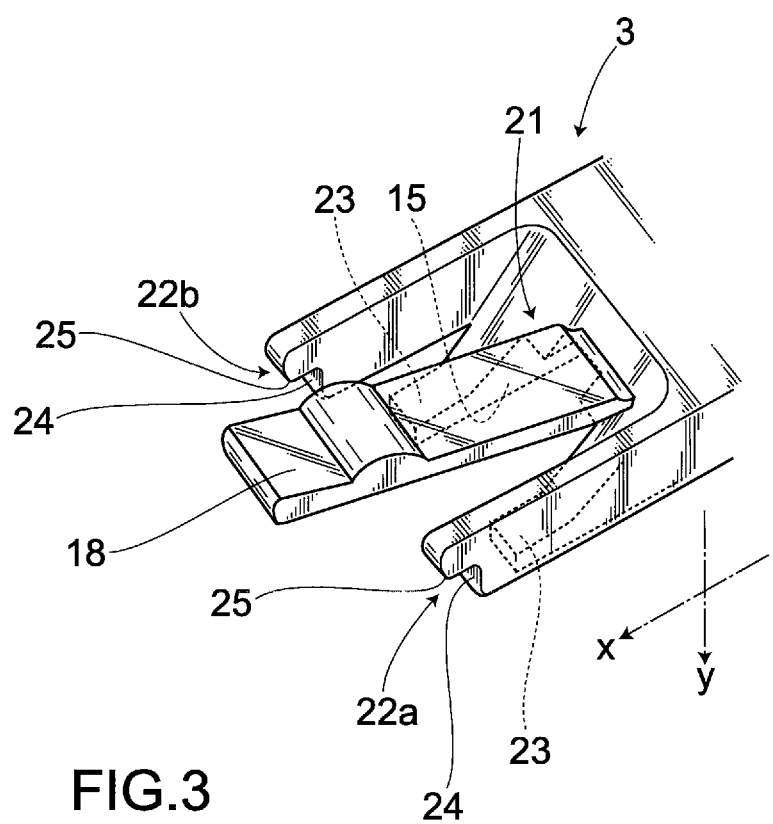
FIG. 3 is a partially enlarged perspective view showing the structure of the slider of the first embodiment of the present invention.

In addition to the structure described so far, the slider 3 of the present embodiment, as shown in FIG. 3, further includes a first abutting portion 21 for pushing up a supporting portion 7 arranged on a rear side with respect to the lens advancement axis A with respect to the optical part 6 (referred to as a rear supporting portion 7*a*, hereunder), and second abutting portions 22*a*, 22*b* abutting against a rear outer edge of the optical part 6.

The first abutting portion 21 has a slanting surface formed in the center of the front end of the slider 3 and slanting toward a direction between the advancement direction x and the direction y. The guiding groove 15 is opened in the center of the first abutting portion 21, and a front end of the plunger 4 is thus allowed to protrude from the guiding groove 15 in the advancement direction x. Further, restriction portions 23 are formed on front ends of the first abutting portion 21. The restriction portions 23 serve to prevent the rear supporting portion 7*a* from entering in between the slider 3 and the main body 2 and thus being damaged, as the rear supporting portion 7*a* deforms in the direction y. According to the present embodiment, the restriction portions 23 protrude from lower ends of the slanting surface to the advancement direction x.

The second abutting portions 22a, 22b are respectively provided on both sides of the first abutting portion 21, and are configured to be able to abut against the outer edge of the optical part 6 of the intraocular lens 5. According to the present embodiment, the second abutting portions 22a, 22b protrude from the front end of the slider 3 to the advancement direction x, and at least 22a is allowed to abut against, along the lens advancement axis A, an outer edge of a section of the optical part 6, such section of the optical part 6 being located outward from a connecting portion of the supporting portion 7 and the optical part 6.

Further, the second abutting portions 22a, 22b have x-direction abutting surfaces 24 and y-direction abutting surfaces 25. The x-direction abutting surfaces 24 are perpendicular to a surface of the optical part 6, and are thus capable of pushing out the outer edge of the optical part 6. The y-direction abutting surfaces 25 are parallel with the surface of the optical part 6, and are thus able to restrict a surface of the optical part 6 in the vicinity of the outer edge thereof from being valley folded before the rear supporting portion 7a has been sufficiently deformed.

As described above, according to the intraocular lens insertion device 1 of the present embodiment, the first abutting portion 21 and the second abutting portions 22a, 22b are provided on the slider 3 allowing the intraocular lens 5 to be in contact therewith through a contact area larger than that of the plunger 4. Accordingly, the motion of the rear supporting portion 7a can be appropriately regulated during the process of moving the intraocular lens 5. Further, there can be reduced the possibility of reoperation being required after the intraocular lens 5 is inserted into the eye.

(3) Operation and Effect

According to the intraocular lens insertion device 1 having the aforementioned structure, the intraocular lens 5 is placed internally in a manner such that the optical part 6 thereof is arranged in parallel with the lens advancement axis A (FIGS. 4A and 4B). The slider 3 is at first moved to the advancement direction x in order to release the intraocular lens 5 internally placed in advance to the outside from the front end of the nozzle section 11. In this way, the first abutting portion 21 formed on the front end of the slider 3 is caused to abut against the rear supporting portion 7a (FIGS. 5A and 5B).

Since the first abutting portion 21 has the slanting surface, the rear supporting portion 7a is pushed up therealong as the slider 3 is further moved to the advancement direction x (FIGS. 6A and 6B). At the same time, the x-direction abutting surfaces 24 of the second abutting portions 22a, 22b are caused to abut against as well as push out the optical part 6, thereby moving the intraocular lens 5 from the lens placement section to the transition section 10. At that time, the outer edge of the optical part 6 is pushed by the inner wall of the transition section 10. Further, the lens pressing member 18 is also pushed by the inner wall of the transition section 10, and is thus caused to push down the surface of the optical part 6 to the direction y. In this way, the optical part 6 of the intraocular lens 5 is valley folded.

Next, as the plunger 4 is moved to the advancement direction x, the front end of such plunger 4 supported by the guiding groove 15 of the slider 3 is caused to abut against the outer edge of the optical part 6 (FIGS. 7A and 7B). The rear supporting portion 7a pushed up by the first abutting portion 21 is thus caused to deform along the plunger 4 in a manner such that a front end of the rear supporting portion 7a eventually points to the advancement direction x. In this way, the front end of the rear supporting portion 7a deformed due to the first abutting portion 21, is tucked into the surface of the valley-folded optical part 6.

Here, the y-direction abutting surfaces 25 of the second abutting portions 22a, 22b are configured to restrict the surface of the optical part 6 in the vicinity of the outer edge thereof from being valley folded, thereby preventing the outer edge of the optical part 6 from interfering with the rear supporting portion 7a during a deformation process of the rear supporting portion 7a. Accordingly, the intraocular lens insertion device 1 allows the rear supporting portion 7a to further reliably enter a space formed by the valley-folded surface of the optical part 6, thereby making it possible to further reliably deform the intraocular lens 5 into the given shape.

Further, the restriction portions 23 provided on the first abutting portion 21 serve to prevent the rear supporting portion 7a from deforming to the direction y. In this sense, the intraocular lens insertion device 1 allows the intraocular lens 5 to be further reliably deformed into the given shape.

Next, by further moving the plunger 4 to the advancement direction x, the intraocular lens 5 is moved from the transition section 10 to the nozzle section 11 (FIGS. 8A and 8B), followed by being released to the outside from the front end of the nozzle section 11 with the intraocular lens 5 itself being folded even smaller.

As described earlier, the intraocular lens insertion device 1 allows the rear supporting portion 7a to be pushed up by the first abutting portion 21, thereby making it possible to appropriately regulate the motion of the rear supporting portion 7a during the process of moving the intraocular lens 5 and reduce the possibility of reoperation being required after the intraocular lens 5 is inserted into the eye.

Further, since the first abutting portion 21 is provided on the slider 3, the rear supporting portion 7a is allowed to come into contact with the first abutting portion 21 through a large contact area. Accordingly, the intraocular lens insertion device 1 of the present embodiment allows the rear supporting portion 7a to be further stably deformed, thereby making it possible to further appropriately regulate the rear supporting portion 7a.

2. Second Embodiment

A second embodiment of the present invention is described hereunder with reference to the accompanying drawings. Here, the second embodiment differs from the first embodiment only in the structure of the front end portion of the slider 3. Therefore, same symbols are used to describe the same members as those in the first embodiment, and the descriptions of the corresponding members are thus omitted for the sake of convenience.

Figure 9:
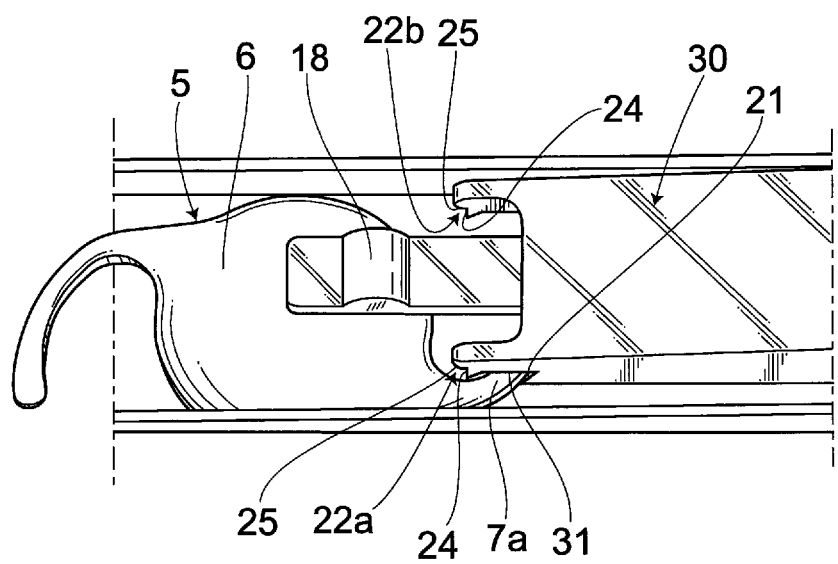
FIG. 9 is a partially enlarged perspective view showing a structure of a slider of a second embodiment of the present invention.

According to a slider 30 shown in FIG. 9, at least 22a of second abutting portions 22a, 22b is configured to abut against an outer edge of a section of the optical part 6 between the connecting portion of the rear supporting portion 7a and the optical part 6, and the lens advancement axis A. Further, this slider 30 has a cutout hole 31 formed on a side surface thereof, such cutout hole 31 allowing the rear supporting portion 7a to be inserted therethrough inwardly from the outside.

According to the present embodiment having the aforementioned structure, the slider 30 is at first moved to the advancement direction x by gripping operation portions 17. As a result, a first abutting portion 21 formed on a front end of the slider 30 is caused to abut against the rear supporting portion 7a.

As the slider 30 is further moved to the advancement direction x, the rear supporting portion 7a is pushed up with x-direction abutting surfaces 24 of the second abutting portion 22 abutting against and pushing out the optical part 6, at the same time, thus allowing the intraocular lens 5 to be moved from a lens placement section to a transition section 10. In this way, the optical part 6 is pushed by an inner wall of the transition section 10, and a surface of the optical part 6 is pushed down to the direction y by means of a lens pressing member 18, thus allowing the optical part 6 to be valley folded (FIGS. 10A and 10B).

Next, as a plunger 4 is moved to the advancement direction x, the front end of such plunger 4 supported by a guiding groove 15 of the slider 3 is caused to abut against the outer edge of the optical part 6 (FIGS. 11A and 11B). The supporting portion 7 pushed up by the first abutting portion 21 is thus caused to deform along the plunger 4 in a manner such that a front end of the supporting portion 7 eventually points to the advancement direction x. In this way, a front end of the supporting portion 7 deformed due to the first abutting portion 21, is tucked into the surface of the valley-folded optical part 6.

Next, by further moving the plunger 4 to the advancement direction x, the intraocular lens 5 is moved from the transition section 10 to a nozzle section 11 (FIGS. 12A and 12B), followed by being released to the outside from a front end of the nozzle section 11 with the intraocular lens 5 itself being folded even smaller.

Due to the aforementioned structure of the present embodiment, the present embodiment, as is the case in the first embodiment, allows the motion of the rear supporting portion 7a to be appropriately regulated during the process of moving the intraocular lens 5, and reduces the possibility of reoperation being required after the intraocular lens 5 is inserted into the eye.

3. Third Embodiment

Figure 13:
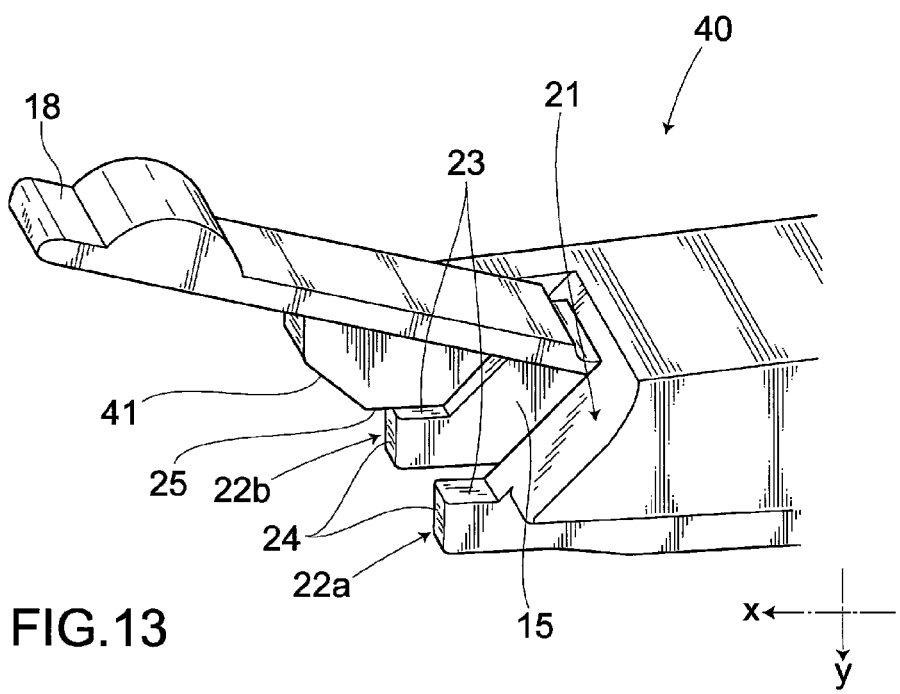
FIG. 13 is a partially enlarged perspective view showing a structure of a slider of a third embodiment of the present invention.

As shown in FIG. 13, a slider 40 of the present embodiment includes a first abutting portion 21, second abutting portions 22a, 22b and a guiding portion 41 for guiding the optical part 6 to the second abutting portion 22b. The second abutting portion 22b is provided on a location opposite to the connecting portion of the rear supporting portion 7a and the optical part 6, and is configured to be able to abut against the optical part 6 or the outer edge thereof. Further, the second abutting portion 22b has an x-direction abutting surface 24 and a y-direction abutting surface 25. In contrast, the second abutting portion 22a only has the x-direction abutting surface 24.

Here, the y-direction abutting surface 25 of the second abutting portion 22b may be arranged substantially on the same plane as restriction portions 23, or beyond the restriction portions 23 in the direction y. According to the present embodiment, the y-direction abutting surface 25 is arranged on the same plane as the restriction portions 23.

Figure 14:
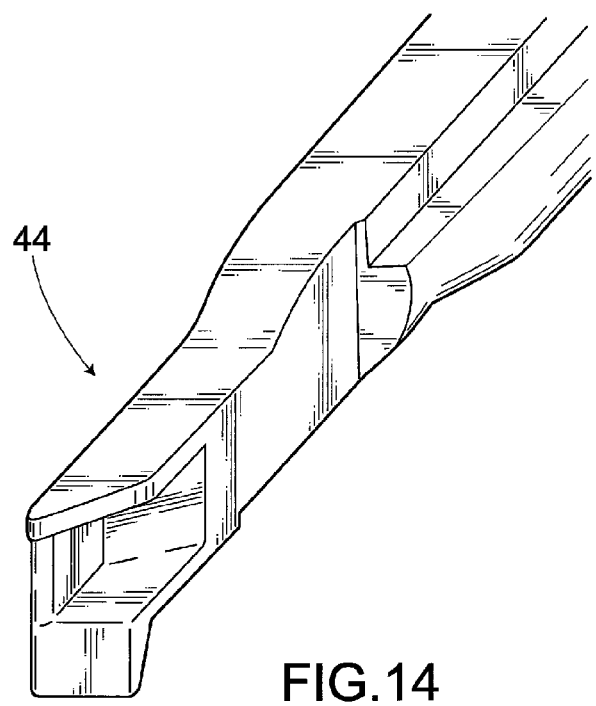
FIG. 14 is a partially enlarged perspective view showing a structure of a plunger of the third embodiment of the present invention.

The guiding portion 41 has a slanting surface slanting toward a direction between the advancement direction x and an opposite direction of the direction y. A lower end of the guiding portion 41 is communicated with the y-direction abutting surface 25. Here, a plunger having a shape shown in FIG. 14 can be used as a plunger 44.

Next, there are described an operation and effect of the slider 40 having the aforementioned structure. The intraocular lens 5 is placed in a lens placement section (not shown) in a manner such that the optical part 6 thereof is arranged in parallel with the lens advancement axis A (FIGS. 15A and 15B). The slider 40 is at first moved to the advancement direction x in order to release such intraocular lens 5 to the outside from a front end of a nozzle section 11. As a result, the first abutting portion 21 formed on a front end of the slider 40 is caused to abut against the rear supporting portion 7a (FIGS. 16A and 16B).

Since the first abutting portion 21 has a slanting surface, the rear supporting portion 7a is pushed up therealong as the slider 40 is further moved to the advancement direction x (FIGS. 17A and 17B). At the same time, the guiding portion 41 serves to push down a surface of the optical part 6 to the direction y, thereby guiding the corresponding optical part 6 to the second abutting portion 22b. As a result, the x-direction abutting surface 24 of the second abutting portion 22b and the x-direction abutting surface 24 of the second abutting portion 22a are caused to abut against and then push out the optical part 6, thus allowing the intraocular lens 5 to be moved from the lens placement section to a transition section 10.

Here, the slider 40 allows the optical part 6 to be guided to the second abutting portion 22b by means of the guiding portion 41, thereby causing the second abutting portion 22b to further reliably abut against the optical part 6, and thus allowing the intraocular lens 5 to be further reliably pushed out.

In this way, the outer edge of the optical part 6 is pushed by an inner wall of the transition section 10. Further, at that time, a lens pressing member 18 is also pushed by the inner wall of the transition section 10, thus pushing down the surface of the optical part 6 to the direction y. As a result, the optical part 6 of the intraocular lens 5 is valley folded.

Next, as the plunger 44 is moved to the advancement direction x, the front end of such plunger 44 supported by a guiding groove 15 of the slider 40 is caused to abut against the outer edge of the optical part 6 (FIGS. 18A and 18B). The rear supporting portion 7a pushed up by the first abutting portion 21 is thus caused to deform along the plunger 44 in a manner such that a front end of the rear supporting portion 7a eventually points to the advancement direction x. In this way, the front end of the rear supporting portion 7a deformed due to the first abutting portion 21, is enclosed by the valley-folded surface of the optical part 6. In other words, the plunger 44 is configured to further bend the rear supporting portion (or "trailing haptic") 7a, such that the free end of the rear support portion is positioned over the optical part 6, as the plunger moves relative to the slider 40 and into contact with the optical part outer edge.

Here, the y-direction abutting surface 25 of the second abutting portion 22b is configured to restrict the surface of the optical part 6 in the vicinity of the outer edge thereof from being valley folded, thereby preventing the outer edge of the optical part 6 from interfering with the rear supporting portion 7a during the deformation process of the rear supporting portion 7a.

Particularly, according to the present embodiment, since the y-direction abutting surface 25 is arranged on the same plane as the restriction portions 23, the outer edge of the optical part 6 is restricted from deforming to the opposite direction of the direction y, particularly, from deforming beyond the restriction portions 23 and the rear supporting portion 7a deformed due to the first abutting portion 21. In this sense, the slider 40 can further reliably prevent the outer edge of the optical part 6 from interfering with the rear supporting portion 7a, thereby allowing the intraocular lens 5 to be further reliably deformed into the given shape.

Next, by further moving the plunger 44 to the advancement direction x, the intraocular lens 5 is moved from a transition section 10 to a nozzle section 11 (FIGS. 19A and 19B), followed by being released to the outside from a front end of the nozzle section 11 with the intraocular lens 5 itself being folded even smaller.

Since the slider 40 of the present embodiment includes the first abutting portion 21 and the restriction portions 23, there can be achieved the same effects as those of the first embodiment.

4. Modified Embodiment

The present invention is not limited to the aforementioned embodiments. As a matter of fact, appropriate modifications are possible within the scope of the gist of the present invention. For example, in each one of the aforementioned embodiments, there are provided two second abutting portions in total. However, the present invention is not limited to this configuration. Particularly, the number of the second abutting portions can be one, three or more than three.

Further, in each one of the aforementioned embodiments, the second abutting portions 22 are provided as a symmetrical pair. However, the present invention is not limited to this configuration. The second abutting portions 22 can actually be provided in an asymmetrical manner. For example, one of the second abutting portions 22 may be formed longer than the other second abutting portion 22 in the advancement direction x, thereby making it possible to slightly rotate the intraocular lens 5 about an optical axis, and thus making it easier to regulate a supporting portion disposed forward.

Description of Symbols 1 intraocular lens insertion device
2 main body
3 slider
4 plunger
5 intraocular lens
6 optical part
7 supporting portion
7a rear supporting portion
21 first abutting portion
22 second abutting portion
x advancement direction
y direction (downward direction)
A lens advancement axis

The invention claimed is:

1. An intraocular lens insertion device, comprising:
a lens placement section;
a nozzle section;
a transition section, having a tapered inner wall, between the lens placement section and the nozzle section;
the lens placement section, transition section and nozzle section defining a lens advancement axis;
an intraocular lens located in the lens placement section and having an optical part with an outer edge, a first support portion that extends outwardly from the optical part outer edge, and a second support portion that extends outwardly from the optical part outer edge, the second support portion being closer to the nozzle section than the first support portion;
a slider, movable relative to the lens placement section, that pushes the intraocular lens along the lens advancement axis in a lens advancement direction out of the lens placement section and into the transition section, the slider including first and second abutting portions spaced from one another in the lens advancement direction by a distance that results in the first abutting portion bending the first support arm toward the optical part when the second abutting portion engages optical part outer edge, the second abutting portion including an x-direction abutting surface having a face substantially perpendicular to a surface of the optical part and a y-direction abutting surface having a face substantially parallel with the surface of the optical part; and
a plunger, movable relative to the slider, that pushes the intraocular lens out of the transition section and through the nozzle section.

2. The intraocular lens insertion device according to claim 1, wherein the second abutting portion comprises a pair of second abutting portions located on opposite sides of the lens advancement axis.

3. The intraocular lens insertion device according to claim 1, wherein the first abutting portion slants downward in the lens advancement direction.

4. The intraocular lens insertion device according to claim 1, further comprising:
a guide that directs the optical part outer edge to the second abutting portion.

5. The intraocular lens insertion device according to claim 2, wherein the pair of second abutting portions are equidistant from the lens advancement axis.

6. The intraocular lens insertion device according to claim 1, wherein
the plunger moves along the lens advancement axis;
the first and second support portions define free ends;
the first abutting portion bends the first support portion to an orientation where the first support portion crosses the lens advancement axis; and
the plunger is configured to further bend the first support portion, such that the free end of the support portion is positioned over the optical part, as the plunger moves relative to the slider and into contact with the optical part outer edge.

7. The intraocular lens insertion device according to claim 1, wherein
the plunger moves along the lens advancement axis;
the first and second support portions define free ends;
the first abutting portion bends the first support arm to an orientation where the first support arm crosses the lens advancement axis; and
the plunger is configured to further bend the first support arm, such that the free end of the support arm is positioned over the optical part and points toward the nozzle section, as the plunger moves relative to the slider and into contact with the optical part outer edge.

8. The intraocular lens insertion device according to claim 1, wherein
the slider includes a pivotable lens pressing member.

9. An intraocular lens insertion device, comprising:
a lens placement section;
a nozzle section;
a transition section, having a tapered inner wall, between the lens placement section and the nozzle section;
the lens placement section, nozzle section and transition section defining a lens advancement axis;
an intraocular lens located in the lens placement section and having an optical part with an outer edge, a leading haptic, and a trailing haptic;
a slider, movable relative to the lens placement section, that pushes the intraocular lens along the lens advancement axis out of lens placement section and into the transition section, the slider including means for folding a portion of the trailing haptic toward the optical part as the slider engages the optical part outer edge; and
a plunger, movable relative to the slider, that pushes the intraocular lens out of the transition section and through the nozzle section.

10. An intraocular lens insertion device as claimed in claim 9, wherein
the plunger includes a surface that engages the optical part outer edge and a protrusion that extends over the optical part outer edge.

11. An intraocular lens insertion device as claimed in claim 9, wherein
the plunger is configured to push the folded portion of the trailing haptic over the optical part as the plunger engages the optical part outer edge.

12. An intraocular lens insertion device as claimed in claim 9, wherein
the trailing haptic includes a free end; and
the plunger is configured to push the folded portion of the trailing haptic over the optical part such that the free end points toward the nozzle section as the plunger engages the optical part outer edge.

13. An intraocular lens insertion device as claimed in claim 9, wherein
the slider includes a pivotable lens pressing member.

* * * * *